United States Patent
Eldin et al.

[11] Patent Number: 5,847,156
[45] Date of Patent: Dec. 8, 1998

[54] POLYMERIZABLE DIKETOPYRROLOPYRROLES AND POLYMERS PREPARED THEREWITH

[75] Inventors: Sameer Hosam Eldin, Courtepin; Abul Iqbal, Arconciel, both of Switzerland

[73] Assignee: Ciba Specialty Chemicals Corporation, Tarrytown, N.Y.

[21] Appl. No.: 789,893

[22] Filed: Jan. 29, 1997

[30] Foreign Application Priority Data

Jan. 3, 1996 [CH] Switzerland ................ 227/96

[51] Int. Cl.$^6$ ............................ C07D 487/04
[52] U.S. Cl. ............... 548/453; 544/328; 544/373; 544/144; 546/276.7; 546/199; 548/335.1; 548/364.7; 548/255; 548/264.8; 548/233; 548/217; 548/159; 548/195
[58] Field of Search ................ 548/453, 335.1, 548/364.7, 255, 264.8; 544/328; 546/276.7

[56] References Cited

U.S. PATENT DOCUMENTS

| | | | |
|---|---|---|---|
| 4,415,685 | 11/1983 | Iqbal et al. | 524/92 |
| 4,579,949 | 4/1986 | Rochat et al. | 546/167 |
| 4,585,878 | 4/1986 | Jost et al. | 548/453 |
| 4,666,455 | 5/1987 | Jost et al. | 8/506 |
| 4,778,899 | 10/1988 | Pfenninger et al. | 548/453 |
| 5,484,943 | 1/1996 | Zambounis et al. | 548/453 |
| 5,527,922 | 6/1996 | Zambounis et al. | 548/453 |
| 5,591,865 | 1/1997 | Hao et al. | 548/453 |
| 5,616,725 | 4/1997 | Zambounis et al. | 548/453 |

FOREIGN PATENT DOCUMENTS

| | | |
|---|---|---|
| 0337951 | 10/1989 | European Pat. Off. . |
| 467846 | 1/1992 | European Pat. Off. . |
| 0704497 | 4/1996 | European Pat. Off. . |
| 0718697 | 6/1996 | European Pat. Off. . |

OTHER PUBLICATIONS

Chan et al. J. Am. Chem. Soc. 1993, 115, pp. 11735–11743.
Derwent Abst. 96–173008[18] (1995).

*Primary Examiner*—Johann Richter
*Assistant Examiner*—Laura R. C. Lutz
*Attorney, Agent, or Firm*—Kevin T. Mansfield

[57] ABSTRACT

1,4-Diketopyrrolopyrroles of the formula

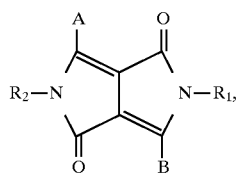

(I)

in which A and B independently of one another are a group of the formula

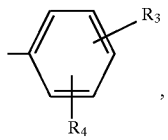

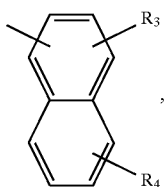

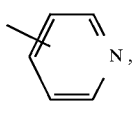

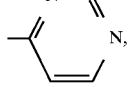

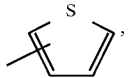

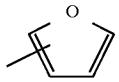

or

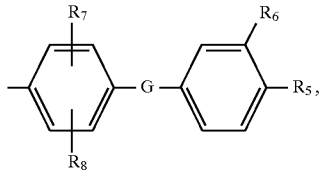

$R_1$ is a long-chain radical containing a reactive group capable of polymerization, and $R_2$ is $C_1$–$C_6$alkyl,

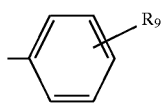

or $R_1$.

The novel diketopyrrolopyrroles are suitable for preparing coloured polymers with unexpectedly advantageous colour effects.

7 Claims, No Drawings

POLYMERIZABLE DIKETOPYRROLOPYRROLES AND POLYMERS PREPARED THEREWITH

The present invention relates to novel diketopyrrolopyrroles containing polymerizable reactive groups, and to polymers prepared therewith.

The diketopyrrolopyrrole pigments which are now referred to in the literature as well, for example in the Colour Index, as DPP pigments, and which have been known for some years and found to be useful, are described inter alia in U.S. Pat. No. 4 415 685 and U.S. Pat. No. 4 579 949.

EP-A 337 951 describes coloured polymer microparticles which can be obtained by copolymerizing pigment derivatives which contain polymerizable reactive groups into various kinds of polymers. Mention is made in this context of derivatives of a wide variety of classes of pigment, including DPP derivatives, and specifically one member thereof, a 1,4-diketo-3,6-diphenylpyrrolo[3,4-c]pyrrole substituted on both nitrogen atoms by an ethyl methacrylate group.

However, it has been found that the copolymerization of this compound does not take place satisfactorily.

It has now been found that it is nevertheless possible, by introducing specific, long-chain reactive groups, to obtain DPP chromophores which, surprisingly, can be reacted readily with polymers or to form polymers, whether directly, by homo- or copolymerization, or else by grafting onto existing, preformed homo- or copolymers.

The present invention accordingly provides 1,4-diketopyrrolopyrroles of the formula

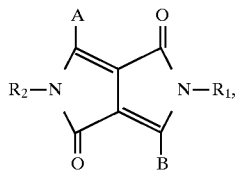

(I)

in which A and B independently of one another are a group of the formula

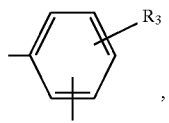

,

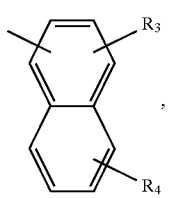

,

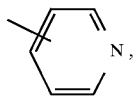

,

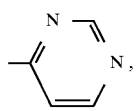

,

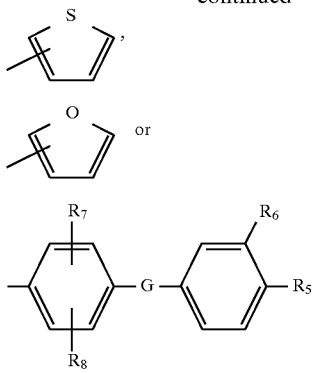

in which
$R_3$ and $R_4$ independently of one another are hydrogen, halogen, $C_1$–$C_{18}$alkyl, $C_1$–$C_{18}$alkoxy, $C_1$–$C_{18}$alkylmercapto, $C_1$–$C_{18}$alkylamino, $C_1$–$C_{18}$alkoxycarbonyl, $C_1$–$C_{18}$alkylaminocarbonyl, —CN, —NO$_2$, trifluoromethyl, $C_5$–$C_6$cycloalkyl, —C=N—($C_1$–$C_{18}$alkyl),

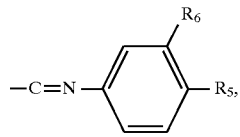

imidazolyl, pyrazolyl, triazolyl, piperazinyl, pyrrolyl, oxazolyl, benzoxazolyl, benzothiazolyl, benzimidazolyl, morpholinyl, piperidinyl or pyrrolidinyl, G is —CH$_2$—, —CH(CH$_3$)—, —C(CH$_3$)$_2$—, —CH=N—, —N=N—, —O—, —S—, —SO—, —SO$_2$—, —CONH— or —NR$_9$—, $R_5$ and $R_6$ independently of one another are hydrogen, halogen, $C_1$–$C_6$alkyl, $C_1$–$C_{18}$alkoxy or —CN, $R_7$ and $R_8$ independently of one another are hydrogen, halogen or $C_1$–$C_6$alkyl and $R_9$ is hydrogen or $C_1$–$C_6$alkyl, $R_1$ is a radical having at least 4 carbon atoms and containing a polymerizable reactive group, and $R_2$ is $C_1$–$C_6$alkyl,

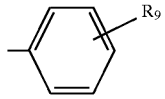

or $R_1$.

the term polymerizable reactive groups refers, for example, to groups capable of addition polymerization, for example acrylate radicals, or groups capable of condensation polymerization, for example hydroxyl or acid chloride groups, or else groups capable of polyaddition, for example hydroxyl or isocyanate groups.

Preferably $R_1$ is a radical of the formula

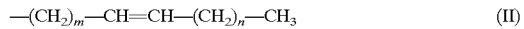

—(CH$_2$)$_m$—CH=CH—(CH$_2$)$_n$—CH$_3$ (II)

or

—(Y)$_p$—X—(Z)$_r$—Q (III)

in which m and n independently of one another are an integer between zero and 12, with the proviso that the sum m+n is at least 4, and p and r independently of one another are zero or 1, X is uninterrupted $C_4$–$C_{18}$alkylene or is $C_4$–$C_{18}$alkylene which is interrupted one or more times by —O— and/or —S—, —NH—, phenylene, —COO—, —CONH— or

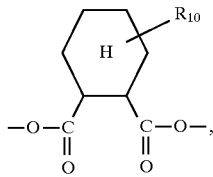

in which $R_{10}$ is hydrogen or methyl,
Y is

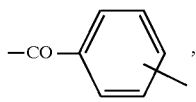

—Si(Cl)$_2$—, —Si(OC$_2$H$_5$)$_2$—, —Si(OCOCH$_3$)$_2$—, —CH$_2$—CH(OH)— or —CH(CN)— and
Z is —O—, —NH—, —COO—, phenylene,

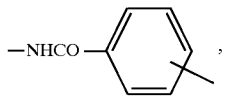

—Si(Cl)$_2$—, —Si(OC$_2$H$_5$)$_2$ — or —Si(OCOCH$_3$)$_2$—,
Q is —OH, —NH$_2$, glycidyl,

—CHO, —NCO, —CH=CH$_2$, —C(CH$_3$)=CH$_2$, —CO—CH=CH$_2$, —CO—C(CH$_3$)=CH$_2$, $C_5$–$C_7$cycloalkenyl,

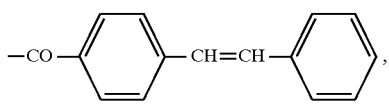

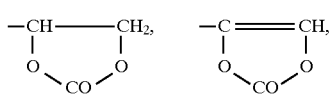

—CONHR$_{11}$, —COOR$_{11}$ or —COR$_{11}$, in which
R$_{11}$ is hydrogen or $C_1$–$C_6$alkyl,
or Q is

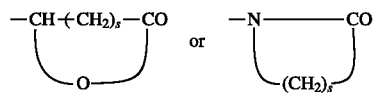

in which s is an integer from 1 to 6 such as 1, 2, 3, 4, 5 or 6.

Any halogen substituents are generally iodine, fluorine, bromine or chlorine, preferably bromine or chlorine, particularly preferably chlorine;

the $C_1$–$C_4$alkyl radical is methyl, ethyl, n-propyl, isopropyl, n-butyl, sec-butyl, isobutyl or tert-butyl;

$C_1$–$C_6$alkyl is, for example, methyl, ethyl, n-propyl, isopropyl, n-butyl, sec-butyl, isobutyl, tert-butyl, n-amyl, tert-amyl or hexyl;

the $C_1$–$C_{18}$alkyl radical is, for example, methyl, ethyl, n-propyl, isopropyl, n-butyl, sec-butyl, isobutyl, tert-butyl, n-amyl, tert-amyl, hexyl, heptyl, octyl, 2-ethylhexyl, nonyl, decyl, dodecyl, tetradecyl, hexadecyl or octadecyl;

$C_4$–$C_{18}$alkylene, preferably the linear representatives, can for example be —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$—, —(CH$_2$)$_{12}$—, —(CH$_2$)$_{13}$—, —(CH$_2$)$_{14}$—, —(CH$_2$)$_{15}$—, —(CH$_2$)$_{16}$—, —(CH$_2$)$_{17}$—, —(CH$_2$)$_{18}$—, preferably $C_4$–$C_{12}$alkylene such as —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$—, or —(CH$_2$)$_{12}$—;

$C_1$–$C_{18}$alkoxy is, both alone and in $C_1$–$C_{18}$alkoxycarbonyl, for example methoxy, ethoxy, n-propoxy, isopropoxy, butyloxy, hexyloxy, decyloxy, dodecyloxy, hexadecyloxy or octadecyloxy, preferably $C_1$–$C_6$alkoxy such as methoxy, ethoxy, n-propoxy, isopropoxy, butyloxy, hexyloxy;

$C_1$–$C_{18}$alkylmercapto is, for example, methylmercapto, ethylmercapto, propylmercapto, butylmercapto, octylmercapto, decylmercapto, hexadecylmercapto or octadecylmercapto;

$C_1$–$C_{18}$alkylamino is, both alone and in $C_1$–$C_{18}$alkylaminocarbonyl, for example methylamino, ethylamino, propylamino, hexylamino, decylamino, hexadecylamino or octadecylamino, preferably $C_1$–$C_6$alkylamino such as methylamino, ethylamino, propylamino or hexylamino.

$C_5$–$C_6$cycloalkyl is, for example, cyclopentyl or cyclohexyl, especially cyclohexyl.

$C_5$–$C_7$cycloalkenyl is mono- or bicyclic cycloalkenyl, for example cyclopentenyl, cyclohexenyl or norbornenyl.

Some examples of $R_1$ as a radical of the formula III are
—(CH$_2$)$_6$—OH, —(CH$_2$)$_{10}$—OH, —(CH$_2$)$_{11}$—OH,
—(CH$_2$)$_6$—OCO—CH=CH$_2$, —(CH$_2$)$_6$—OCO—C(CH$_3$)=CH$_2$,
(CH$_2$)$_{10}$—OCO—CH=CH$_2$, —(CH$_2$)$_{10}$—OCO—C(CH$_3$)=CH$_2$, —(CH$_2$)$_{11}$—OCO—CH=CH$_2$,
—(CH$_2$)$_{11}$—OCO—C(CH$_3$)=CH$_2$,
—(CH$_2$)$_2$—O—(CH$_2$)$_2$—O—(CH$_2$)$_2$—OH
—(CH$_2$)$_2$—O—(CH$_2$)$_2$—O—(CH$_2$)$_2$—O—CO—CH=CH$_2$
—(CH$_2$)$_2$—O—(CH$_2$)$_2$—O—(CH$_2$)$_2$—O—CO—C(CH$_3$)=CH$_2$

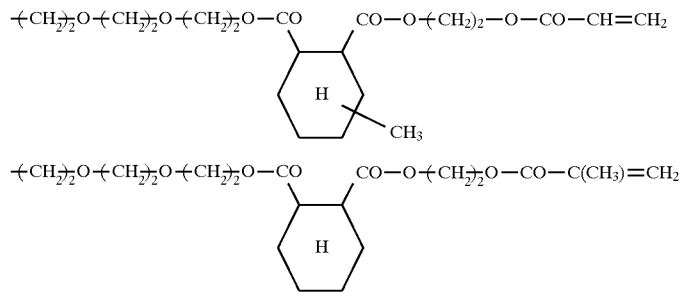

—(CH$_2$)$_3$—S—(CH$_2$)$_2$—OH
—(CH$_2$)$_3$—S—(CH$_2$)$_6$—OH
—(CH$_2$)$_3$—S—(CH$_2$)$_2$—COOH
—(CH$_2$)$_3$—S—(CH$_2$)$_6$—COOH
—(CH$_2$)$_3$—S—(CH$_2$)$_2$—NH$_2$
—(CH$_2$)$_3$—S—(CH$_2$)$_6$—NH$_2$
—(CH$_2$)$_3$—S—(CH$_2$)$_2$—O—(CH$_2$)$_2$—O—(CH$_2$)$_2$—OH
—(CH$_2$)$_3$—S—(CH$_2$)$_2$—O—(CH$_2$)$_2$—O—(CH$_2$)$_2$—NH$_3$

—CH$_2$—C$_6$H$_4$—(CH$_2$)$_2$S(CH$_2$)$_2$OH
—CH$_2$—C$_6$H$_4$—(CH$_2$)$_2$S(CH$_2$)$_6$OH
—CH$_2$—C$_6$H$_4$—(CH$_2$)$_2$S(CH$_2$)$_2$COOH
—CH$_2$—C$_6$H$_4$—(CH$_2$)$_2$S(CH$_2$)$_2$NH$_2$
—CH$_2$—C$_6$H$_4$—(CH$_2$)$_2$S(CH$_2$)$_6$NH$_2$
—CH$_2$—C$_6$H$_4$—(CH$_2$)$_2$S(CH$_2$)$_2$O(CH$_2$)$_2$O(CH$_2$)$_2$OH
—CH$_2$—C$_6$H$_4$—(CH$_2$)$_2$S(CH$_2$)$_2$O(CH$_2$)$_2$O(CH$_2$)$_2$NH$_2$

—C(O)—C$_6$H$_4$—(CH$_2$)$_2$S(CH$_2$)$_2$OH
—C(O)—C$_6$H$_4$—(CH$_2$)$_2$S(CH$_2$)$_6$OH
—C(O)—C$_6$H$_4$—(CH$_2$)$_2$S(CH$_2$)$_2$COOH
—C(O)—C$_6$H$_4$—(CH$_2$)$_2$S(CH$_2$)$_6$COOH
—C(O)—C$_6$H$_4$—(CH$_2$)$_2$S(CH$_2$)$_2$NH$_2$
—C(O)—C$_6$H$_4$—(CH$_2$)$_2$S(CH$_2$)$_6$NH$_2$

-continued

—C(O)—C$_6$H$_4$—(CH$_2$)$_2$S(CH$_2$)$_2$O(CH$_2$)$_2$O(CH$_2$)$_2$OH
—C(O)—C$_6$H$_4$—(CH$_2$)$_2$S(CH$_2$)$_2$O(CH$_2$)$_2$O(CH$_2$)$_2$NH$_2$

—(CH$_2$)$_6$—O—Si(Cl)$_2$—CH=CH$_2$
—(CH$_2$)$_6$—O—Si(OC$_2$H$_5$)$_2$—CH=CH$_2$
—(CH$_2$)$_6$—O—Si(O—COCH$_3$)$_2$—CH=CH$_2$
—Si(Cl)$_2$—(CH$_2$)$_2$—S—(CH$_2$)$_2$—OH
—Si(Cl)$_2$—(CH$_2$)$_2$—S—(CH$_2$)$_6$—OH
—Si(Cl)$_2$—(CH$_2$)$_2$—S—(CH$_2$)$_2$—COOH
—Si(Cl)$_2$—(CH$_2$)$_2$—S—(CH$_2$)$_2$—NH$_2$
—Si(Cl)$_2$—(CH$_2$)$_2$—S—(CH$_2$)$_6$—NH$_2$
—Si(Cl)$_2$—(CH$_2$)$_2$—S—(CH$_2$CH$_2$O)$_2$—CH$_2$CH$_2$OH
—Si(Cl)$_2$—(CH$_2$)$_2$—S—(CH$_2$CH$_2$O)$_2$—CH$_2$CH$_2$NH$_2$
—Si(OC$_2$H$_5$)$_2$—(CH$_2$)$_2$—S—(CH$_2$)$_2$—OH
—Si(OC$_2$H$_5$)$_2$—(CH$_2$)$_2$—S—(CH$_2$)$_6$—OH
—Si(OC$_2$H$_5$)$_2$—(CH$_2$)$_2$—S—(CH$_2$)$_2$—COOH
—Si(OC$_2$H$_5$)$_2$—(CH$_2$)$_2$—S—(CH$_2$)$_6$—COOH
—Si(OC$_2$H$_5$)$_2$—(CH$_2$)$_2$—S—(CH$_2$)$_2$—NH$_2$
—Si(OC$_2$H$_5$)$_2$—(CH$_2$)$_2$—S—(CH$_2$)$_6$—NH$_2$
—Si(OC$_2$H$_5$)$_2$—(CH$_2$)$_2$—S—(CH$_2$CH$_2$O)$_2$—CH$_2$CH$_2$OH
—Si(OC$_2$H$_5$)$_2$—(CH$_2$)$_2$—S—(CH$_2$CH$_2$O)$_2$—CH$_2$CH$_2$NH$_2$
—Si(OCOCH$_3$)$_2$—(CH$_2$)$_2$—S—(CH$_2$)$_2$—OH
—Si(OCOCH$_3$)$_2$—(CH$_2$)$_2$—S—(CH$_2$)$_6$—OH
—Si(OCOCH$_3$)$_2$—(CH$_2$)$_2$—S—(CH$_2$)$_2$—COOH
—Si(OCOCH$_3$)$_2$—(CH$_2$)$_2$—S—(CH$_2$)$_6$—COOH
—Si(OCOCH$_3$)$_2$—(CH$_2$)$_2$—S—(CH$_2$)$_2$—NH$_2$
—Si(OCOCH$_3$)$_2$—(CH$_2$)$_2$—S—(CH$_2$)$_6$—NH$_2$
—Si(OCOCH$_3$)$_2$—(CH$_2$)$_2$—S—(CH$_2$CH$_2$O)$_2$—CH$_2$CH$_2$OH
—Si(OCOCH$_3$)$_2$—(CH$_2$)$_2$—S—(CH$_2$CH$_2$O)$_2$—CH$_2$CH$_2$NH$_2$
—CH$_2$CH(OH)—CH$_2$—S—(CH$_2$)$_6$—COOH
—CH$_2$CH(OH)—CH$_2$—S—(CH$_2$)$_6$—OH
—CH$_2$CH(OH)—CH$_2$—S—(CH$_2$CH$_2$O)$_2$—CH$_2$CH$_2$OH
—CH$_2$CH(OH)—CH$_2$—S—(CH$_2$CH$_2$O)$_2$—CH$_2$CH$_2$COOH
—CH$_2$CH(OH)—CH$_2$—NH—(CH$_2$)$_6$—COOH
—CH$_2$CH(OH)—CH$_2$—NH—(CH$_2$)$_6$—OH
—CH$_2$CH(OH)—CH$_2$—NH—(CH$_2$CH$_2$O)$_2$—CH$_2$CH$_2$OH

—CH$_2$—CONH—(CH$_2$)$_6$—OH

—CH$_2$—CONH—(CH$_2$)$_6$—COOH

—CH$_2$—CONH—(CH$_2$CH$_2$O)$_2$—CH$_2$CH$_2$OH

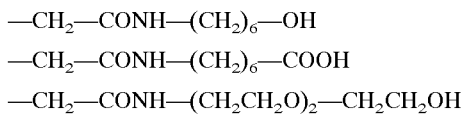

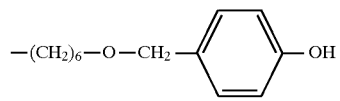

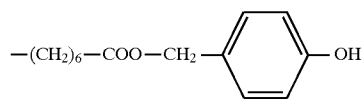

—CH(CN)—(CH$_2$)$_6$—OH

—CH(CN)—(CH$_2$CH$_2$O)$_2$—CH$_2$CH$_2$OH

—(CH$_2$)$_6$—O—CH$_2$CH$_2$O—CH=CH$_2$

—(CH$_2$)$_6$—O—CH$_2$—CH=CH$_2$

—(CH$_2$)$_6$—O—CH=CH$_2$

—(CH$_2$)$_6$—O—CH$_2$—CO—CH=CH$_2$

—(CH$_2$)$_6$—O—CO—CH=CH$_2$

—(CH$_2$)$_6$—O—(CH$_2$)$_2$—NHCO—CH=CH$_2$

—(CH$_2$)$_6$—O—CH$_2$—COO—CH=CH$_2$

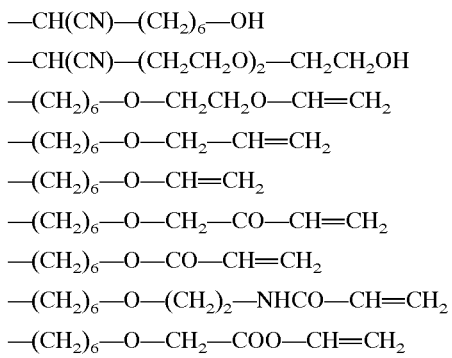

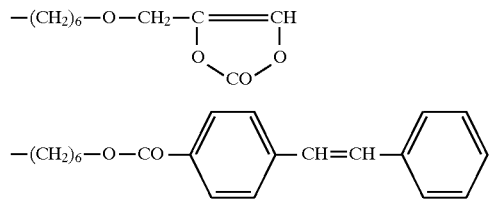

—(CH$_2$)$_6$—O—CH$_2$—CHO

—(CH$_2$)$_6$—O—CH$_2$—NCO

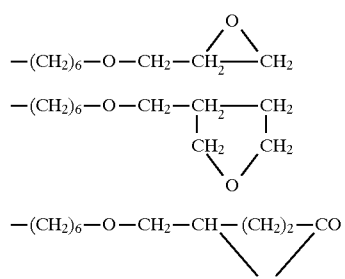

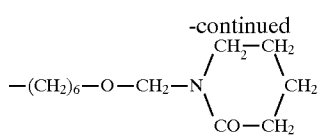

—(CH$_2$)$_3$—S—(CH$_2$)$_2$—CO—O—CO—CH$_3$.

Of particular interest are the novel diketopyrrolopyrroles of the formula I in which A and B independently of one another are a group of the formula

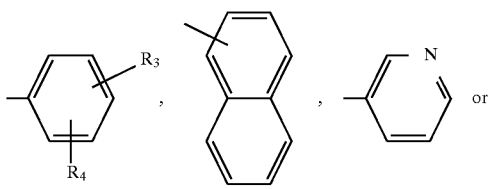

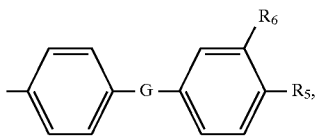

in which R$_3$ and R$_4$ independently of one another are hydrogen, halogen such as chlorine or bromine, C$_1$–C$_4$alkyl, C$_1$–C$_6$alkoxy, C$_1$–C$_6$alkylamino or CN, G is —O—, —NR$_9$—, —N=N— or —SO$_2$—, R$_5$ and R$_6$ are hydrogen, and R$_9$ is hydrogen, methyl or ethyl, and especially those in which, in the formula I, A and B are identical and are a group of the formula

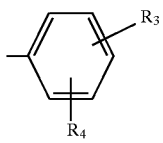

in which R$_3$ and R$_4$ independently of one another are hydrogen, methyl, tert-butyl, chlorine, bromine or CN. R$_4$ is preferably hydrogen.

Of particular significance are those novel diketopyrrolopyrroles of the formula I in which R$_1$ is a radical of the formula —X—(O)$_r$—Q          (IV)

in which

X is uninterrupted C$_4$–C$_{12}$alkylene or is C$_4$–C$_{12}$alkylene which is interrupted 1, 2 or 3 times by O and/or once by —S—, —NH— or

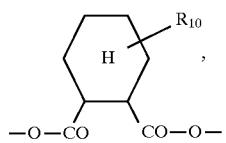

r and R$_{10}$ are as defined above, and

Q is —OH; —CH=CH$_2$, —C(CH$_3$)=CH$_2$, —CO—CH=CH$_2$ or —CO—C(CH$_3$)=CH$_2$.

X is preferably —(CH$_2$)$_q$—, where q can be an integer between 6 and 12, such as 6, 7, 8, 9, 10, 11 or 12, —(CH$_2$CH$_2$O)$_2$—CH$_2$CH$_2$—, or

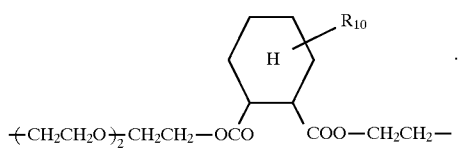

R$_2$ is preferably CH$_3$ or R$_1$, subject to the same preferences as for R$_1$.

The novel diketopyrrolopyrroles of the formula I in which R$_1$ is a radical of the formula II or III and R$_2$ is C$_1$–C$_6$alkyl or

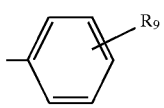

which are preferably prepared by reacting a pyrrolinone of the formula

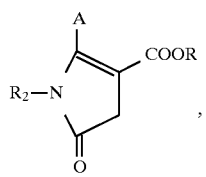 (V)

in which R is preferably C$_1$–C$_4$alkyl, with a nitrile of the formula

B—CN (VI)

where A and B are as defined above, to give the diketopyrrolopyrrole of the formula

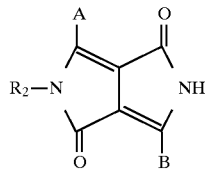

which is reacted further with a compound of the formula

R$_1$—Hal (VII)

or, if Y in the radical with the formula III is —CH$_2$—CH(OH)—, with a compound of the formula

 (VIII)

in which R$_1$, X, Z, r and r are as defined above and Hal is preferably chlorine or bromine.

The reaction parameters can be chosen, for example, in analogy to the method described in U.S. Pat. No. 4,778,899 and consequently further details on this subject are unnecessary.

Novel diketo pyrroles of the formula I in which R$_1$ and R$_2$ are identical are obtained analogously, in a preferred embodiment, starting from a diketopyrrolopyrrole of the formula

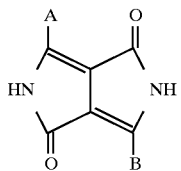 (IX)

(obtainable, for example, by the method described in U.S. Pat. No. 4,579,949) using corresponding amounts of the compounds of the formulae VII and VIII.

Diketopyrrolopyrroles of formula I in which Q for example is —CO—CH=CH$_2$ or —CO—C(CH$_3$)=CH$_2$ and r is 1 can be prepared, in a further preferred embodiment, by reacting diketopyrrolopyrroles of the formula I in which Q is —OH with acryloyl chloride or methacryloyl chloride, respectively. In a similar manner it is also possible, for example, to introduce the groups —Si(Cl)$_2$—CH=CH$_2$, —Si(OC$_2$H$_5$)$_2$—CH=CH$_2$, —Si(OCOCH$_3$)$_2$—CH=CH$_2$, —CONHR$_{11}$, —COOR$_{11}$, etc., as Q or Z—Q respectively.

Pyrrolinones of the formula V are conventionally obtained by methods known per se, for example by cyclizing a compound of the formula

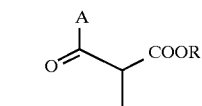 (X)

in which A and R are as defined above, with an ammonium salt, to give the pyrrolinone of the formula

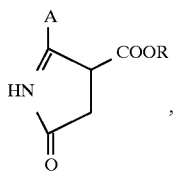

as described, for example, in U.S. Pat. No. 4 778 899, and reacting it further with a compound of the formula R$_2$—Hal, in which R$_2$ is C$_1$–C$_6$alkyl or

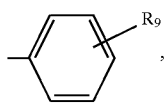

in accordance with generally known methods.

The compounds of the formulae VI, VII, VII, IX and X are known and/or can be prepared in analogy to generally known techniques.

The novel DPP compounds can be used very readily, by virtue of their reactive groups, for preparing or modifying polymers by a polymerization reaction or a polymer-analogous reaction. The coloured polymers modified or prepared in this way unexpectedly exhibit advantageous colour effects and—depending on the amount of DPP compound used—a wide variety of shades, which may differ entirely from those of the corresponding DPP pigments which possess no groups capable of polymerization.

The present invention provides, furthermore, a process for preparing or modifying polymers by polymerization or polymer-analogous reaction, which involves polymerizing a diketopyrrolopyrrole of the formula I, in the presence if desired of an appropriate, preferably customary comonomer, for example one carrying at least one carbon-carbon double bond, or of a polymer which carries polymerizable groups.

In a preferred embodiment of this invention coloured (co)polymers can be prepared by polyreacting a mixture of the novel DPP momoners and further customary and suitable monomers in a liquid phase, e.g. in a melt, solution, suspension or emulsion.

These novel DPP polymers are commonly prepared in accordance with generally known methods, for example either by a polymerization reaction, i.e. by addition polymerization (thermal or photochemical), condensation polymerization or polyaddition, or by a polymer-analogous reaction, i.e. by reacting the novel DPP compounds, containing suitable reactive groups, with existing polymers which themselves have reactive groups (grafting).

In accordance with observations made to date, the novel DPP compounds (DPP monomers) can be used to conduct all known types of polymerization reaction. Thus it is possible, for example, to use DPP monomers whose reactive groups have C=C bonds to prepare vinyl, allyl, vinyl ester, vinyl amide, vinyl acetate or vinyl ketone polymers; to use monofunctional DPP monomers whose reactive groups contain heteroatoms to prepare polyaldehydes, polyisocyanates, polyepoxides, polyethers, polyacetones or polylactams; to use bifunctional DPP monomers whose reactive groups contain heteroatoms to prepare polyesters, polyamides, polyimides or polycarbonates by way of condensation polymerization, and polyepoxides, polyurethanes or polyimides by way of polyaddition, it being possible for the polymerization to involve free-radical, cationic or anionic polymerization, coordination polymerization or group-transfer polymerization.

Examples of the preparation of DPP polymers, starting from the novel DPP monomers, include:

Addition polymerization: DPP polyacrylates by free-radical thermal polymerization of DPP acrylates; DPP polyacrylates by free-radical photopolymerization of DPP acrylates.

Condensation polymerization: DPP polyesters from DPP diols and di-acid chlorides; DPP polycarbonates from DPP diols and phosgene.

Polyaddition: DPP polyurethanes from DPP diols and diisocyanates; DPP polyepoxides from DPP epoxides and amines.

Polymer-analogous reaction: Reaction of a DPP alcohol with a polymer which has been prepared from styrene and maleic anhydride, and thus contains anhydride groups, to form a polymer containing DPP mono- or diester groups.

The novel DPP polymers may also include additives, such as light stabilizers, antioxidants and UV absorbers, which can be added during or after actual polymerization, also for example during the processing of the polymers (extrusion). These additives may themselves also have polymerizable reactive groups, and in this case can be copolymerized together with the DPP monomers.

The DPP polymers prepared in accordance with this invention and which hereinafter will be understood as including also copolymers prepared from novel DPP polymers and other customary monomers, are advantageously suited to many purposes, such as for colouring high molecular weight organic materials, e.g. biopolymers, plastic materials, including fibres, glasses, ceramic products, for formulations in decorative cosmetics, for the preparation of inks, printing inks, paint systems, in particular automotive lacquers and photoresists, photo- and electroconductive polymers, fluorescent whitening agents, photocell aggregates, coloured photoresists and dispersion colours and, furthermore, the novel diketopyrrolo-pyrroles can be used in the biomedical field of application, e.g. for the preparation of diagnostic agents as well as in the fields of impact-printing and non-impact-printing and photo/repro in general.

Illustrative examples of suitable organic materials of high molecular weight which can be coloured with the DPP polymers of this invention are vinyl polymers, for example poly-styrene, poly-α-methylstyrene, poly-p-methylstyrene, poly-p-hydroxystyrene, poly-p-hydroxy-phenylstyrene, polymethyl methacrylate and polyacrylamide as well as the corresponding methacrylic compounds, polymethylmaleate, polyacrylonitrile, polymethacrylonitrile, poly-vinyl chloride, polyvinyl fluoride, polyvinylidene chloride, polyvinylidene fluoride, polyvinyl acetate, polymethyl vinyl ether and polybutyl vinyl ether; polymers which are derived from maleinimide and/or maleic anhydride, such as copolymers of maleic anhydride with styrene; polyvinyl pyrrolidone; ABS; ASA; polyamides; polyimides; polyamidimides; polysulfones; polyether sulfones; polyphenylene oxides; polyurethanes; polyureas; polycarbonates; polyarylenes; polyarylene sulfides; polyepoxides; polyolefins such as polyethylene and polypropylene; polyalkadienes; biopolymers and the derivatives thereof e.g. cellulose, cellulose ethers and esters such as ethylcellulose, nitrocellulose, cellulose acetate and cellulose butyrate, starch, chitin, chitosan, gelatine, zein; natural resins; synthetic resins such as alkyd resins, acrylic resins, phenolic resins, epoxide resins, aminoformaldehyde resins such as urea/formaldehyde resins and melamine/formaldehyde resin; vulcanized rubber; casein; silicone and silicone resins; rubber, chlorinated rubber; and also polymers which are used, for example, as binders in paint systems, such as novolaks which are derived from $C_1$–$C_6$-aldehydes such as formaldehyde and acetaldehyde and a binucluear or mononuclear, preferably mononuclear, phenol which, if desired, is substituted by one or two $C_1$–$C_9$alkyl groups, one or two halogen atoms or one phenyl ring, such as o-, m- or p-cresol, xylene, p-tert-butylphenol, o-, m- or p-nonylphenol, p-chlorophenol or p-phenylphenol, or a compound having more than one phenolic group such as resorcinol, bis(4-hydroxyphenyl)-methane or 2,2-bis(4-hydroxyphenyl)propane; as well as suitable mixtures of said materials.

Particularly preferred high molecular weight organic materials, in particular for the preparation of a paint system, a printing ink or ink, are, for example, cellulose ethers and esters, e.g. ethylcellulose, nitrocellulose, cellulose acetate and cellulose butyrate, natural resins or synthetic resins (polymerization or condensation resins) such as aminoplasts, in particular urea/formaldehyde and melamine/formaldehyde resins, alkyd resins, phenolic plastics, polycarbonates, polyolefins, polystyrene, polyvinyl chloride, polyamides, polyurethanes, polyester, ABS, ASA, polyphenylene oxides, vulcanized rubber, casein, silicone and silicone resins as well as their possible mixtures with one another.

It is also possible to use high molecular weight organic materials in dissolved form as film formers, for example boiled linseed oil, nitrocellulose, alkyd resins, phenolic resins, melamine/formaldehyde and urea/formaldehyde resins as well as acrylic resins.

Said high molecular weight organic compounds may be obtained singly or in admixture, for example in the form of granules, plastic materials, melts or in the form of solutions, in particular for the preparation of spinning solutions, paint systems, coating materials, inks or printing inks.

In a particularly preferred embodiment of this invention, the novel DPP polymers are used for the mass coloration of polyvinyl chloride, polyamides and, especially, polyolefins such as polyethylene and polypropylene as well as for the preparation of paint systems, including powder coatings, inks, printing inks and coating colours.

Illustrative examples of preferred binders for paint systems are alkyd/melamine resin paints, acryl/melamine resin paints, cellulose acetate/cellulose butyrate paints and two-pack system lacquers based on acrylic resins which are crosslinkable with polyisocyanate. According to observations made to date, the novel DPP polymers can be added in any desired amount to the material to be coloured, depending on the end use requirements. In the case of high molecular weight organic materials, for example, the pigments composed according to this invention can be used in an amount in the range from 0.01 to 40, preferably from 0.1 to 20% by weight, based on the total weight of the coloured high molecular weight organic material.

The pigmenting of the high molecular weight organic materials with the novel DPP polymers is usually effected by incorporating said novel DPP polymers, if desired in the form of masterbatches, in the high molecular weight organic materials using customary apparatus suitable to this end, such as extruders, roll mills, mixing or milling apparatus. The material thus treated is then normally brought into the desired final form by methods which are known per se, such as calendering, moulding, extrusion moulding, coating, casting, extruding, or by injection moulding.

In a preferred embodiment of this invention, the novel DPP monomers can be polyreacted in an extruder together with other monomers, in particular with those monomers which are customarily used for the preparation of the aforementioned polymers (reactive extrusion, for example in general accordance with the process disclosed in EP-A 337 951). Copolymers prepared in this manner usually have the same spectrum of application as the blends so far cited consisting of novel DPP polymers and high molecular weight organic materials.

To produce non-brittle mouldings or to diminish their brittleness, so-called plasticizers can be added to the high molecular weight substances prior to moulding. Plasticizers may be, for example, esters of phosphoric acid, phthalic acid and sebacic acid. Said plasticizers may be added before, during or after pigmenting the high molecular weight substances with the DPP polymers of this invention.

To obtain different shades, the novel DPP polymers may advantageously be used in admixture with fillers, transparent and opaque white, coloured and/or black pigments as well as customary luster pigments in the desired amount.

For the preparation of paints systems, coating materials, inks and printing inks, the corresponding high molecular weight organic substances, such as binders, synthetic resin dispersions etc. and the novel DPP polymers are usually dispersed or dissolved together, if desired together with customary additives such as fillers, paint auxiliaries, siccatives, plasticizers and/or additional pigments, in a common solvent or mixture of solvents. This can be achieved by dispersing or dissolving the individual components by themselves, or also several components together, and only then bringing all components together, or by adding everything together at once.

For application in printing, all customary industrial printing processes can be employed, such as screen printing, rotogravure, bronze printing, flexographic printing and off-set printing.

The Examples which follow illustrate the invention. Preparation of DPP monomers

EXAMPLE 1a):

29.8 g (0.12 mol) of the pyrrolinone of the formula

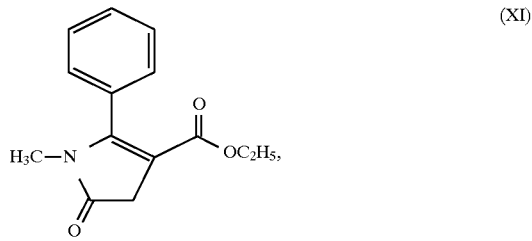

(XI)

prepared in accordance with the method described in Example 4 of U.S. Pat. No. 4,778,899, and 18.16 g (0.132 mol) of p-chlorobenzonitrile are placed in a sulfonating flask, with nitrogen flushing, and 180 ml of 2-methyl-1-pentanol are added. The mixture is heated at 110°–115° C. until, after about 30 minutes, a clear, light brown solution is formed. Subsequently, 12.96 g (0.24 mol) of 30% sodium methylate in saturated sodium hydroxide solution are metered in over the course of 2 hours at a stirring speed of 510–520 rpm, with simultaneous removal, by distillation, of the methanol/ethanol mixture which is formed. Stirring is continued at the same temperature for about one hour, and the mixture is then cooled to room temperature. Following the addition of 500 ml of methanol, the mixture is acidified with 57.7 g (0.96 mol) of acetic acid. Vigorous stirring of the thick slurry which forms produces, after about 3 minutes, an intensely orange-red coloured precipitate. This product is diluted with a further 100 ml of methanol and with 150 ml of water, and the orange-red suspension is filtered. The filter cake is washed with 150 ml of methanol in 3 portions and dried overnight at 60°–70° C. in a vacuum oven, to give 25.53 g (63.2% of theory) of the diketopyrrolopyrrole of the formula

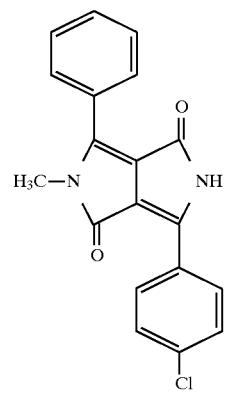

(XII)

| Analysis: | C | H | N | Cl |
|---|---|---|---|---|
| calculated: | 67.76% | 3.89% | 8.32% | 10.53% |
| found: | 67.62% | 3.93% | 8.26% | 10.47% | b) 10.10 g (0.030 mol) of the diketopyrrolopyrrole of the formula XII (Example 1a), 2.50 g (0.018 mol) of potassium carbonate and 100 ml of dimethylacetamide are placed in a sulfonating flask, with nitrogen flushing, and the mixture is heated with stirring at 130°–135° C. After 30 minutes at this temperature, a strongly dark red-brown suspension is obtained to which 7.23 g (0.0375 mol) of 10-chloro-1-decanol, diluted with 10 ml of dimethylacetamide, are added dropwise over the course of 1 hour. After this mixture has been stirred at the same temperature for 4 hours, a further 2.90 g (0.015 mol) of 10-chloro-1-decanol, diluted with 10 ml of dimethylacetamide, are added dropwise over the course of 15 minutes, and stirring is continued, under continual nitrogen flushing, for 4 hours more before the mixture is cooled to room temperature. The dark red-brown solution is subsequently filtered off cold, the filter residue is washed three times with 5 ml of dimethylacetamide, and the filtrate is concentrated to dryness in a rotary evaporator. The crude product is purified by means of column chromatography over silica gel 60 using 9:1 toluene/dioxane as eluent, to give 6.25 g (42.3%) of the compound of the formula

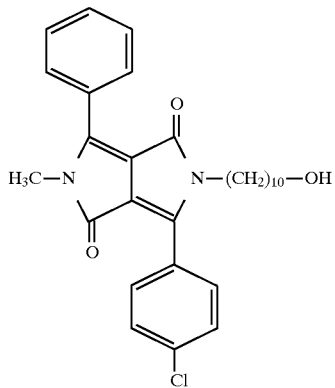

(XIII)

as a dark red oil.

The NMR spectrum in CDCl$_3$/p.a. agrees completely with the target structure.

EXAMPLE 2

In a sulfonating flask thoroughly flushed with nitrogen, 26.94 g (0.08 mol) of the diketopyrrolopyrrole of the formula XII (Example 1a) and 26.85 g (0.195 mol) of potassium carbonate (both substances dried at 350° C. beforehand) are weighed out, and 350 ml of dimethylformamide are added. The mixture is heated with stirring to 120°–125° C., and then 50.50 g (0.195 mol) of 97% 11-bromo-1-undecanol, and dissolved in 100 ml of dimethylformamide, are added dropwise at this temperature over the course of 15 minutes. After the end of addition, a dark red-brown suspension is left which is stirred further at 120°–125° C. for 2 hours and is then cooled to room temperature, during which the colour changes to yellow-brown. This suspension is stirred further at room temperature overnight before being filtered, and the filter residue is washed with 30 ml of dimethylformamide. The filtrate is concentrated to dryness in a rotary evaporator. The crude product is purified by means of column chromatography over silica gel 60 using 8:2 toluene/dioxane as eluent, to give 9.4 g (23.2% of theory) of the compound of the formula

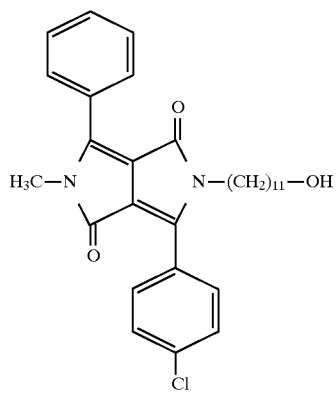

(XIV)

The NMR spectrum in CDCl$_3$/ p.a. agrees with the target structure.

EXAMPLE 3

Under nitrogen, 6.73 g (0.012 mol) of the diketopyrrolopyrrole of the formula XIV (Example 2), 0.012 g (0.06 mmol) of phenothiazine and 110 ml of dichloroethane are placed in a sulfonating flask. The yellow-red solution produced is heated to reflux temperature, and then 2.17 g (0.024 mol) of acryloyl chloride dissolved in 10 ml of dichloroethane are added dropwise over the course of 15 minutes. After the end of the addition, the mixture is stirred further at reflux (80° C.) for 7 hours and then cooled to room temperature. The orange-red solution is extracted in a separating funnel by shaking 5 times with 30 ml of 5% sodium hydroxide solution and then 2 times with deionized water. The organic phase is dried over MgSO$_4$•H$_2$O and filtered. After complete concentration of the orange-red filtrate in a rotary evaporator, the crude product is recrystallized from 60 ml of methanol, to give 6.1 g (81.9% of theory) of an orange-coloured product of the formula

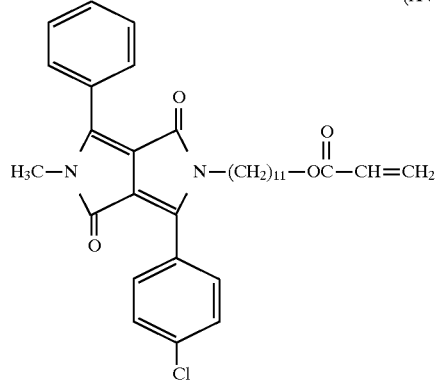

(XV)

| Analysis: | C | H | N | Cl |
| --- | --- | --- | --- | --- |
| calculated: | 70.64% | 6.5% | 4.99% | 6.32% |
| found: | 70.30% | 6.81% | 5.10% | 6.38% |

EXAMPLE 4a)

Under nitrogen, 29.43 g (0.12 mol) of the pyrrolinone of formula XI (Example 1a) and 21.02 g (0.132 mol) of 4-tert-butylbenzonitrile are placed in a sulfonating flask, and 180 ml of 2-methyl-1-pentanol are added. The mixture is then heated with stirring to 115°–120° C. until, after about 30 minutes, a clear, light brown solution is produced. Subsequently, 43.22 g (0.24 mol) of 30% sodium methylate in saturated sodium hydroxide solution are metered in over the course of 2 hours at a stirring speed of 510–520 rpm, with subsequent removal, by distillation, of the methanol/ ethanol mixture which forms. After the end of addition of the sodium methylate, a dark violet solution is produced which is subsequently stirred at 115°–120° C. for 30 minutes and then cooled to room temperature. Following the addition of 600 ml of methanol, the mixture is acidified with 57.7 g of acetic acid and diluted with 600 ml of water. Within the green-yellow solution, a dark oil is formed from which an orange pigment crystallizes out by overnight stirring. This pigment is filtered off, washed several times with methanol, and dried at 40°–50° C. in a vacuum oven, to give 3.84 g of a red-orange crystalline product of the formula

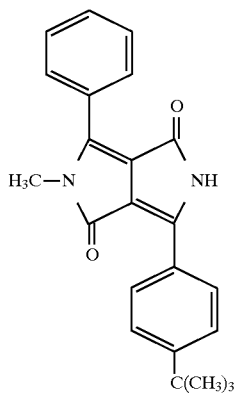

(XVI)

b) The procedure of Example 1b is repeated but replacing the diketopyrrolopyrrole of the formula XII by the equivalent amount of the diketopyrrolopyrrole of the formula XVI, to give the compound of the formula

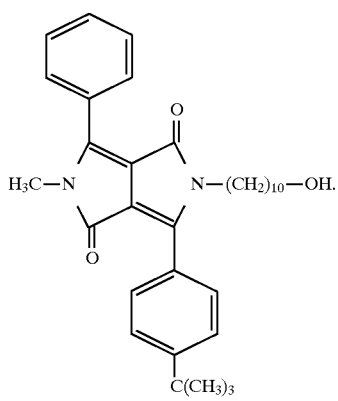

(XVII)

EXAMPLE 5

The procedure of Example 1b is repeated but replacing the 10-chloro-1-decanol by the by the equivalent amount of 6-chloro-1-hexanol, to give the compound of the formula

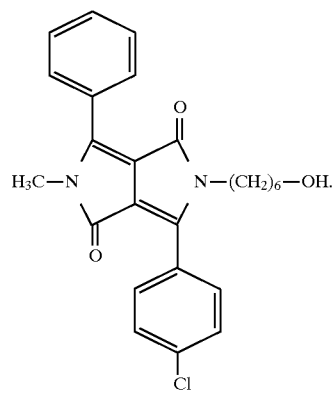

(XVIII)

EXAMPLE 6

20.21 g (0.060 mol) of the diketopyrrolopyrrole of the formula XII (Example 1a) are weighed out directly into a sulfonating flask which is flushed thoroughly with nitrogen, and then 270 ml of dimethylformamide are added, and the mixture is heated at 130°–135° C. with stirring and with nitrogen being supplied. After 30 minutes, 12.44 g (0.090 mol) of potassium carbonate (dried at 250° C.) are added. 15.18 g (0.090 mol) of triethylene glycol monohydrin dissolved in 30 ml of dimethylformamide are added dropwise over the course of 15 minutes to the dark violet suspension. The resulting dark brown suspension is stirred at 130°–135° C. for 4½ hours, then cooled to room temperature and stirred further overnight. It is subsequently filtered, and the filter residue is washed with dimethylformamide. The filtrate is concentrated in a rotary evaporator to a volume of about 150 ml. The product crystallizes out, and is recrystallized from 200 ml of ethanol and dried at 40°–50° C. in a vacuum oven, to give 8.42 g (30% of theory) of a crystalline product of the formula

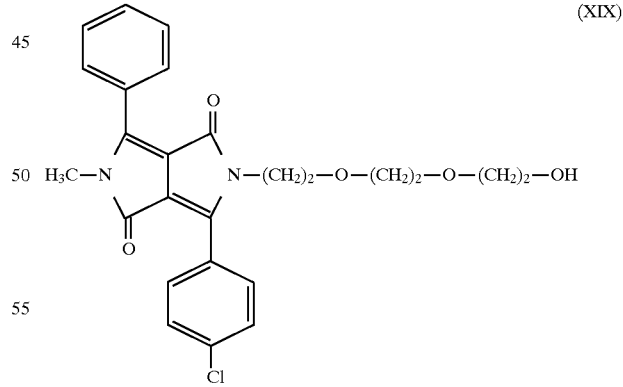

(XIX)

with a melting point of 163° C.

EXAMPLES 7–9

If, in a manner similar to that described in Example 3, a diketopyrrolopyrrole of the formula

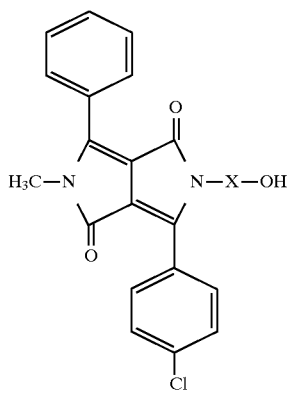

is reacted with an acid chloride of the formula

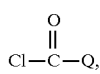

then a product of the formula

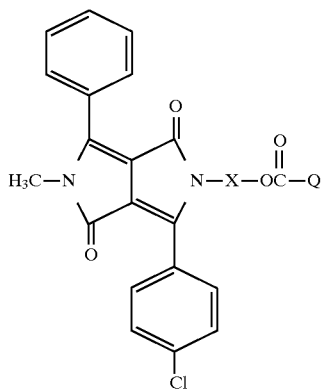

is obtained in which X and Q are as defined in the table below:

| Example | X | Q |
|---|---|---|
| 7 | —(CH$_2$)6— | —C(CH$_3$)=CH$_2$ |
| 8 | —(CH$_2$)10— | —CH=CH$_2$ |
| 9 | —(CH$_2$)2—O—(CH$_2$)$_2$—O—(CH$_2$)$_2$— | —CH=CH$_2$ |

EXAMPLE 10

2.35 g (0.005 mol) of the diketopyrrolopyrrole of the formula XIX (Example 6) and 30 ml of dichlorobenzene are placed under nitrogen in a sulfonating flask, 5.0 mg (0.05 mmol) of thiodiphenylamine are added, and the mixture is heated with stirring at 110°–115° C. 3.17 g (0.010 mol) of the methyl-hexahydrophthalic acid derivative (isomer mixture) of the formula

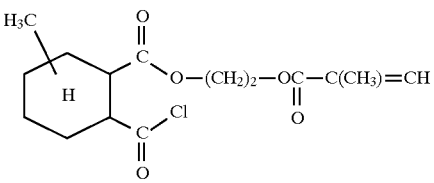

(obtained by generally known methods from methylhexahydrophthalic anhydride and hydroxyethyl methacrylate) are added dropwise with vigorous stirring over the course of 15 minutes to the clear orange-red solution, stirring is continued for about 2 hours at 110°–115° C., and then the mixture is cooled to room temperature. The clear dark red solution is washed in a separating funnel 3 times with 20 ml of 5% sodium hydroxide solution and 2 times with 30 ml of deionized water, and the organic phase is dried over MgSO$_4$•H$_2$O, filtered and concentrated to dryness under a high vacuum. The resulting product is recrystallized from 30 ml of ethanol, to give 3.05 g (81.3% of theory) of a crystalline product of the formula

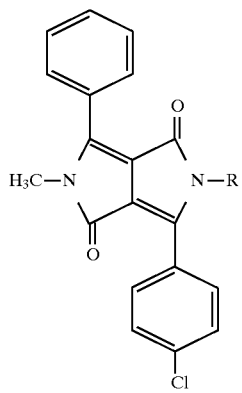

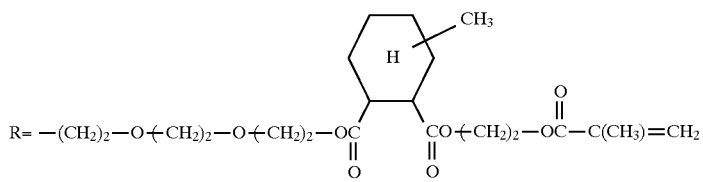

with a melting point of 69.6° C.

EXAMPLE 11

34.60 g (0.12 mol) of diketopyrrolopyrrole of the formula

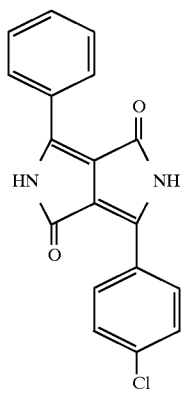

(obtained by the method described in U.S. Pat. No. 4,579,949 (Ex. 26)), 49.76 g (0.36 mol) of potassium carbonate (dried at 350° C.) and 600 ml of freshly distilled dimethylformamide are placed under nitrogen in a sulfonating flask and are heated to 130°–135° C. Then 51.80 g (0.36 mol) of 95% 6-chloro-1-hexanol are added dropwise at this temperature with vigorous stirring over the course of about 10 minutes. After the end of the addition, the dark red suspension is stirred further at 130°–135° C. for 2 hours more and then at room temperature overnight. The resulting dark red solution containing suspended material (KCl, $K_2CO_3$) is filtered and the filter cake is washed three times with 25 ml of dimethylformamide. The filtrate is added with further stirring to 2 l of distilled water, and an orange-coloured product precipitates. The mixture is heated at boiling and filtered at 94° C. The tacky red mass which remains in the filter is dissolved hot in 800 ml of ethanol, and the solution is concentrated to about 300 ml and left to stand overnight, during which an orange-coloured product is precipitated which, after cooling in ice-water, is filtered off and recrystallized from ethanol, to give 15.1 g (26.5% of theory) of an orange crystalline product of the formula (XII)

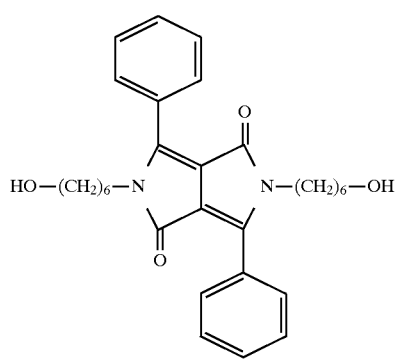

| Analysis: | C | H | N |
|---|---|---|---|
| calculated: | 73.74% | 7.43% | 5.73% |
| found: | 73.51% | 7.47% | 5.66% |

EXAMPLE 12

19.55 g (0.04 mol) of the product from Example 11, 0.04 g ($2 \cdot 10^{-4}$ mol) of phenothiazine and 380 ml of dichloroethane are placed under nitrogen in a sulfonating flask, and the mixture is heated to reflux. The cloudy, orange-coloured solution is treated by dropwise addition, over the course of about 30 minutes under reflux (80° C.) and with stirring, of 14.48 g (0.16 mol) of acryloyl chloride. After the end of the addition, washing is carried out with 20 ml of dichloroethane. The yellow-orange solution is stirred at reflux for 7 hours and then cooled to room temperature and left to stand overnight. The orange-red, very slightly cloudy solution is washed in a separating funnel 5 times with 100 ml of 5% sodium hydroxide solution and 2 times with deionized water, dried over $MgSO_4 \cdot H_2O$ and filtered. The clear, orange-red filtrate is evaporated completely in a rotary evaporator. The red oil which remains solidifies overnight to form a solid mass which is recrystallized from ethanol, to give 23.1 g (96.7% of theory) of a crystalline product of the formula

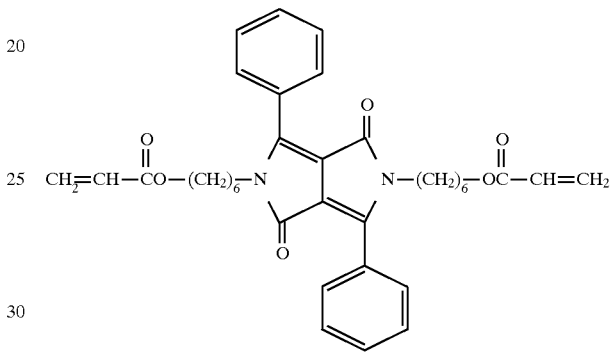

with a melting point of 79.7°–80.1 ° C.

Preparation of DPP polymers

EXAMPLE 13

5.13 g (0.01 mol) of the product from Example 11 and 60 ml of chlorobenzene are placed under nitrogen in a sulfonating flask and heated to reflux. At 120° C. a further 30 ml of chlorobenzene are added. 1.68 g (0.01 mol) of hexamethylene diisocyanate are added dropwise over the course of 15 minutes, with stirring and at 130° C. to the slightly cloudy solution. About 40 minutes after the end of the addition, with the temperature unchanged, a clear solution is present. After a reaction time of 75 minutes, 0.013 g of dimethylcyclohexylamine (1.0 mol % solution in chlorobenzene) is added as catalyst. After a further 3½ hours, the solution changes into a fine suspension. This suspension is stirred overnight at 129° C. and then cooled to room temperature. The orange-red suspension is filtered and the product is dried in vacuo at 60°–70° C., to give 6.3 g (92.5% of theory) of the desired polyurethane with a sharply defined melting point of 142.8° C. The IR (KBr disc) clearly shows the characteristic urethane band at 2330 $cm^{-1}$.

EXAMPLE 14

Photocuring of a DPP bisacrylate monomer 0.8 g of the product from Example 12 is mixed at 60° C. with 7.2 g of Cibatool®SL 5154 (a blend comprising acrylate monomers, photoinitiator and sensitizer, CIBA-GEIGY AG), and the orange-red solution obtained is degassed in vacuo.

Using an Erichsen triangular film-drawing device, films approximately 100 μm thick are drawn out onto glass and are then exposed, using a Hoenle UV lamp from a distance of 20 cm at the 60% setting.

| Exposure time (min.) | Assessment |
|---|---|
| 1 | The film is still liquid |
| 2 | orange-yellow film, still soft |
| 3 | orange-yellow solid film, partially soluble in DMF* |
| 5 | orange-yellow solid film, partially soluble in DMF* |
| 10 | orange-yellow solid film, slightly soluble in DMF* |
| 15 | orange-yellow solid film insoluble in DMF*! |
| 30 | orange-yellow solid film insoluble in DMF*! |

*DMF = dimethylformamide

On the basis of the decrease in solubility, the above table clearly shows that the DPP bisacrylate in this formulation has polymerized completely after 15 minutes.

What is claimed is:

1. A 1,4-diketopyrrolopyrrole of the formula

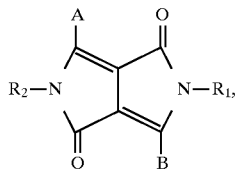 (I)

in which A and B independently of one another are a group of the formula

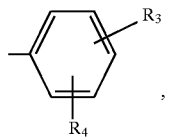,

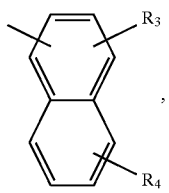,

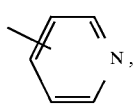,

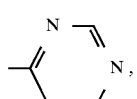,

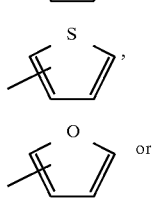,

 or

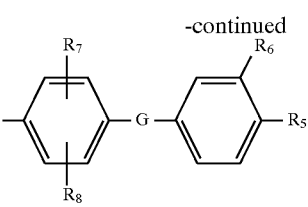

in which $R_3$ and $R_4$ independently of one another are hydrogen, halogen, $C_1$–$C_{18}$alkyl, $C_1$–$C_{18}$alkoxy, $C_1$–$C_{18}$alkylmercapto, $C_1$–$C_{18}$alkylamino, $C_1$–$C_{18}$alkoxycarbonyl, $C_1$–$C_{18}$alkylaminocarbonyl, —CN, —NO$_2$, trifluoromethyl, $C_5$–$C_6$cycloalkyl, —C=N—($C_1$–$C_{18}$alkyl),

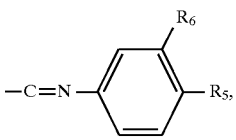

imidazolyl, pyrrazolyl, triazolyl, piperazinyl, pyrrolyl, oxazolyl, benzoxazolyl, benzothiazolyl, benzimidazolyl, morpholinyl, piperidinyl or pyrrolidinyl, G is —CH$_2$—, —CH(CH$_3$)—, —C(CH$_3$)$_2$—, —CH=N—, —N=N—, —O—, —S—, —SO—, —SO$_2$—, —CONH— or —NR$_9$—, $R_5$ and $R_6$ independently of one another are hydrogen, halogen, $C_1$–$C_6$alkyl, $C_1$–$C_{18}$alkoxy or —CN, $R_7$ and $R_8$ independently of one another are hydrogen, halogen or $C_1$–$C_6$alkyl and $R_9$ is hydrogen or $C_1$–$C_6$alkyl, $R_1$ is a radical of the formula

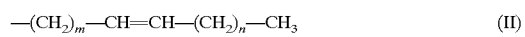 (II)

or

 (III)

in which m and n independently of one another are an integer between zero and 12, with the proviso that the sum m+n is at least 4, and p and r independently of one another are zero or 1, X is uninterrupted $C_4$–$C_{18}$alkylene or is $C_4$–$C_{18}$alkylene which is interrupted one or more times by —O— and/or —S—, —NH—, phenylene, —COO—, —CONH— or

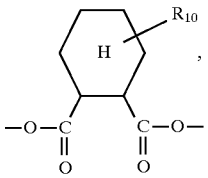

in which $R_{10}$ is hydrogen or methyl,

Y is

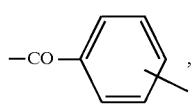

—Si(Cl)$_2$—, —Si(OCOCH$_3$)$_2$—, —CH$_2$—CH(OH)— or —CH(CN)— and

Z is —O—, —NH—, —COO—, phenylene,

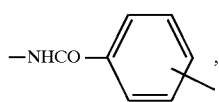

—Si(Cl)$_2$—, —Si(OC$_2$H$_5$)$_2$— or —Si(OCOCH$_3$)$_2$—,

Q is —OH, —NH$_2$, glycidyl,

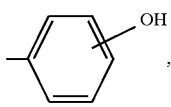

—CHO, —NCO, —CH=CH$_2$, —(CH$_3$)=CH$_2$, —CO—CH=CH$_2$,

—CO—C(CH$_3$)=CH$_2$, C$_5$–C$_7$cycloalkenyl,

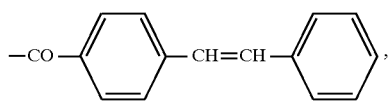

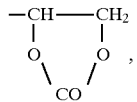

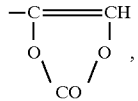

—CONHR$_{11}$, —COOR$_{11}$ or —COR$_{11}$, in which R$_{11}$ is hydrogen or C$_1$–C$_6$alkyl, or Q is

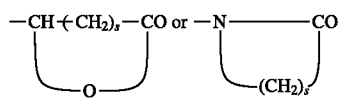

in which s is an integer from 1 to 6, and

R$_2$ is C$_1$–C$_6$alkyl,

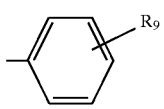

or R$_1$.

2. A diketopyrrolopyrrole according to claim 1, wherein, in the formula I, A and B independently of one another are a group of the formula

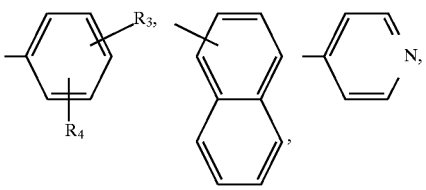

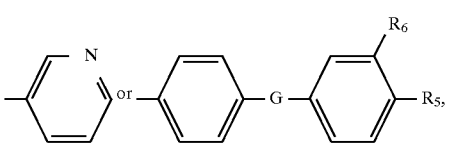

in which R$_3$ and R$_4$ independently of one another are hydrogen, halogen, C$_1$–C$_4$alkyl, C$_1$–C$_6$alkoxy, C$_1$–C$_6$alkylamino or CN, G is —O—, —NR$_9$—, —N=N— or —SO$_2$—, R$_5$ and R$_6$ are hydrogen, and R$_9$ is hydrogen, methyl or ethyl.

3. A diketopyrrolopyrrole according to claim 2, wherein, in the formula I, A and B are identical and are a group of the formula

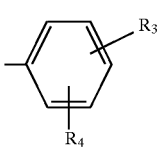

in which R$_3$ and R$_4$ independently of one another are hydrogen, methyl, tert-butyl, chlorine, bromine or CN.

4. A diketopyrrolopyrrole according to claim 1, wherein, in the formula I, R$_1$ is a radical of the formula —X—(O)$_r$—Q  (IV)

in which

X is uninterrupted C$_4$–C$_{12}$alkylene or is C$_4$–C$_{12}$alkylene which is interrupted 1, 2 or 3 times by O and/or once by —S—, —NH— or

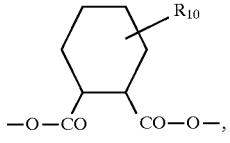

r and R$_{10}$ are as defined in claim 1, and

Q is —OH; —CH=CH$_2$, —C(CH$_3$)=CH$_2$, —CO—CH=CH$_2$ or —CO—C(CH$_3$)=CH$_2$.

5. A diketopyrrolopyrrole according to claim 4, wherein X is —(CH$_2$)$_q$—, where q can be an integer between 6 and 12,

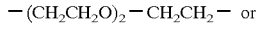

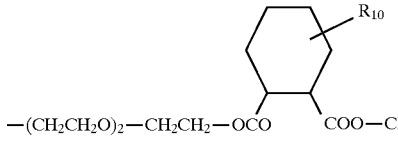

6. A process for preparing a diketopyrrolopyrrole according to claim 1 by reacting a pyrrolinone with a nitrile, which comprises (a) reacting a pyrrolinone of the formula

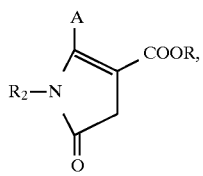  (V)

in which R is $C_1$–$C_4$alkyl, with a nitrile of the formula

B—CN  (VI), where A and B are as defined in claim 1, $R_1$ is a radical of formula —$(CH_2)_m$—CH=CH—$(CH_2)_n$—$CH_3$  (II)

or

—$Y)_p$—X—$(Z)_r$—Q  (III)

in which m and n independently of one another are an integer between zero and 12, with the proviso that the sum m+n is at least 4, and p and r independently of one another are zero or 1, X is uninterrupted $C_4$–$C_{18}$alkylene or is $C_4$–$C_{18}$alkylene which is interrupted one or more times by —O— and/or —S—, —NH—, phenylene, —COO—, —CONH— or

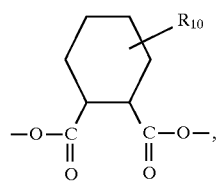

in which $R_{10}$ is hydrogen or methyl,

Y is

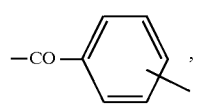

—Si(Cl)—, —Si($OC_2H_5$)$_2$—, —Si(OCOCH$_3$)$_2$—, —$CH_2$—CH(OH)— or —CH(CN)— and Z is —O—, —NH—, —COO—, phenylene,

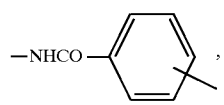

—Si(Cl)$_2$—, —Si($OC_2H_5$)$_2$— or —Si(OCOCH$_3$)$_2$—,

Q is —OH, —$NH_2$, glycidyl,

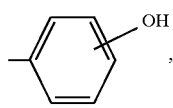

—CHO, —NCO, —CH=$CH_2$, —C(CH)=$CH_2$, —CO—CH=$CH_2$,

—CO—C($CH_3$)=$CH_2$, $C_5$–$C_7$cycloalkenyl,

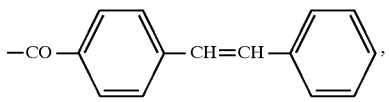

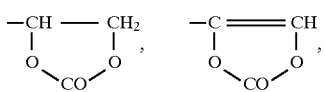

—CONHR$_{11}$, —COOR$_{11}$ or —COR$_{11}$, in which $R_{11}$ is hydrogen or $C_1$–$C_6$alkyl.

or Q is

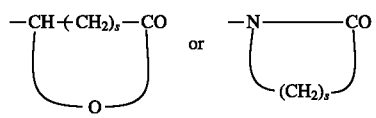

in which s is an integer from 1 to 6, and $R_2$ is $C_1$–$C_6$alkyl or

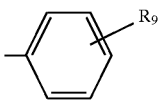

as defined in claim 1, and (a1) reacting diketopyrrolopyrrole with a compound of the formula $R_1$—Hal  (VII)

or, if Y in the radial where the formula III is —$CH_2$—CH(OH)—, with a compound of the formula

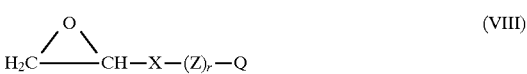  (VIII)

in which $R_1$, X, Z, Q and r are as defined above and Hal is chlorine or bromine, or (a2) reacting a diketopyrrolopyrrole of the formula

  (IX)

with the formulae VII and VIII, in a manner corresponding to that in (a1), or (b) reacting a diketopyrrolopyrrole of the formula I in which $R_1$ is a radical of the formula III as defined above, where Q is —OH, with acryloyl chloride or methacryloyl chloride.

7. A diketopyrrolopyrrole according to claim 1 in which $R_3$ and $R_4$ independently of one another are chlorine or bromine.

* * * * *

UNITED STATES PATENT AND TRADEMARK OFFICE
CERTIFICATE OF CORRECTION

PATENT NO. : 5,847,156
DATED : DECEMBER 8, 1998
INVENTOR(S) : SAMEER HASAM ELDIN ET AL..

It is certified that error appears in the above-identified patent and that said Letters Patent is hereby corrected as shown below:

On the title page, section [30] should read:

-- [30]    Foreign Application Priority Data

January 30, 1996  [CH]  Switzerland          227/96 --.

Signed and Sealed this

Sixth Day of July, 1999

Attest:

Q. TODD DICKINSON

*Attesting Officer*    Acting Commissioner of Patents and Trademarks